US008293800B2

(12) United States Patent
Meier et al.

(10) Patent No.: US 8,293,800 B2
(45) Date of Patent: Oct. 23, 2012

(54) QUINONE DERIVATIVE 2,3-DIMETHOXY-5-METHYL-6-(10-HYDROXYDECYL)-1,4-BENZOQUINONE FOR THE TREATMENT OF PRIMARY PROGRESSIVE MULTIPLE SCLEROSIS

(75) Inventors: Thomas Meier, Basel (CH); Bibiana Bielekova, Kensington, MD (US); Henry F. McFarland, Gaithersburg, MD (US)

(73) Assignees: Santhera Pharmaceuticals (Schweiz) AG, Liestal (CH); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 12/768,930

(22) Filed: Apr. 28, 2010

(65) Prior Publication Data
US 2010/0280130 A1 Nov. 4, 2010

Related U.S. Application Data

(60) Provisional application No. 61/174,170, filed on Apr. 30, 2009.

(30) Foreign Application Priority Data

Apr. 30, 2009 (EP) .................................... 09006030

(51) Int. Cl.
*A61K 31/12* (2006.01)

(52) U.S. Cl. ........................ 514/689; 514/678
(58) Field of Classification Search .................. None
See application file for complete search history.

(56) References Cited

U.S. PATENT DOCUMENTS

2010/0093677 A1 * 4/2010 Goodhew ...................... 514/167
2010/0129431 A1 * 5/2010 Schwarz et al. .............. 424/450

FOREIGN PATENT DOCUMENTS

WO WO 2006/100017 A1 9/2006
WO WO 2008/150509 A1 12/2008

OTHER PUBLICATIONS

Leary et al., "Primary Progressive Multiple Sclerosis Current and Future Treatment Options", CNS Drugs, 2005, 19(5): 369-376 ("Leary").*
Bosco et al., Nuova Rivista di Neurologia, 7(3): 90-94 (Jan. 1, 1997).*
Leary et al., "Primary Progressive Multiple Sclerosis Current and Future Treatment Options", CNS Drugs, 2005, 19(5): 369-376.*
DiProspero, et al., "Neurological effects of high-dose idebenone in patients with Friedreich's ataxia: a randomised, placebo-controlled trial," *Lancet Neurol*, 6: 878-886 (2007).
European Patent Office, Extended European Search Report in European Patent Application No. 09006030.2 (Aug. 4, 2009).
Peyser, et al., "Trial of $d$-$\alpha$-Topopherol in Huntington's disease," *Am. J. Psychiatry*, 152(12): 1771-1775, (1995).
Ranen, et al., "A controlled trial of idebenone in Huntington's disease," *Movement Disorders*, 11(5): 549-554 (1996).
Thal, et al., "Idebenone treatment fails to slow cognitive decline in Alzheimer's disease," *Neurology*, 61: 1498-1502 (2003).
Weyer, et al., "A controlled study of 2 doses of idebenone in the treatment of Alzheimer's disease," *Neuropsychobiology*, 36: 73-82 (1997).
Leary et al., *CNS Drugs*, 19(5): 369-376 (Jan. 1, 2005).

* cited by examiner

*Primary Examiner* — Shengjun Wang
*Assistant Examiner* — Svetlana M Ivanova
(74) *Attorney, Agent, or Firm* — Leydig, Voit & Mayer, Ltd.

(57) ABSTRACT

The present invention relates to approaches, methods, pharmaceuticals and uses directed to the curative treating or preventing of Primary Progressive Multiple Sclerosis (PP-MS), by using 2,3-dimethoxy-5-methyl-6-(10-hydroxydecyl)-1,4-benzoquinone (Idebenone) as the active agent.

12 Claims, 2 Drawing Sheets

QUINONE DERIVATIVE 2,3-DIMETHOXY-5-METHYL-6-(10-HYDROXYDECYL)-1,4-BENZOQUINONE FOR THE TREATMENT OF PRIMARY PROGRESSIVE MULTIPLE SCLEROSIS

CROSS-REFERENCE TO RELATED APPLICATIONS

This patent application claims priority to U.S. Provisional Patent Application No. 61/174,170, filed Apr. 30, 2009.

The present invention relates to approaches, methods, pharmaceuticals and uses directed to the curative treating or preventing of primary progressive multiple sclerosis (PP-MS) by using 2,3-dimethoxy-5-methyl-6-(10-hydroxydecyl)-1,4-benzoquinone (Idebenone) as the active agent.

BACKGROUND OF THE INVENTION

Idebenone is a synthetic, small molecule analogue of coenzyme Q10 (CoQ10), the vital cell membrane antioxidant and essential constituent of the adenosine-triphosphate (ATP)-producing mitochondrial electron transport chain (ETC). Idebenone has the ability to operate under low oxygen tension situations. Due to its ability to inhibit lipid peroxidation, idebenone protects cell membranes and mitochondria from oxidative damage (Zs.-Nagy I (1990) Chemistry, toxicology, pharmacology and pharmacokinetics of idebenone: a review. Arch. Gerontol. Geriatr. 11:177-186). It's antioxidant properties protect against cerebral ischemia and nerve damage in the central nervous system. More importantly, Idebenone also interacts with the ETC, preserving ATP formation in ischemic states. This compound is already used as a nootropic drug and has also been shown to stimulate nerve growth factor, a characteristic that could be important in the treatment of Alzheimer's and other neurodegenerative diseases. Idebenone is described in the specification of Japanese Patent Examined Publication No. 3134/1987 filed by Takeda Chemical Industries, Ltd. In addition it has been shown that idebenone can be applied in the treatment of diseases associated with iron overload, particularly Friedreich Ataxia (U.S. Pat. No. 6,133,322).

As a lipophilic compound Idebenone is well absorbed in the gastrointestinal tract after conventional oral administration, which is the normal route for administering said compound. Dosage forms such as tablets or capsules have been used in clinical trials and as marketed product. In WO 2008/019769 the pharmacological profile of conventionally administered Idebenone is described and the authors suggest to use Idebenone in a transmucosal formulation.

Multiple sclerosis (MS) is an inflammatory and demyelinating disorder of the central nervous system (CNS) that destroys myelin, oligodendrocytes, axons and neurons (Noseworthy, J. H., C. Lucchinetti, et al. (2000). Multiple sclerosis. N Engl J Med 343(13): 938-52). The vast majority of newly-diagnosed MS patients develop the relapsing-remitting form of the disease (RRMS), in which periods of neurological worsening are followed by periods of spontaneous remission, at least at the beginning of the disease process. About 10-15% of patients develop primary progressive MS (PP-MS), characterized by progressive accumulation of neurological disability from the disease onset, without any superimposed worsening (i.e. relapses) or improvements (remissions) (Miller, D. H., S. M. Leary (2007). Primary-progressive multiple sclerosis. Lancet Neurol 6(10): 903-12).

Primary progressive MS (PP-MS) patients differ from RRMS patients in several important characteristics: They tend to be older at the time of disease onset (mean 40 vs. 30 years); males and females tend to be affected equally; clinically there is a high prevalence of cortico-spinal dysfunction characterized by progressive weakness and spasticity; patients have more prominent involvement of the spinal cord (Bieniek, M., D. R. Altmann, et al. (2006). Cord atrophy separates early primary progressive and relapsing remitting multiple sclerosis. J Neurol Neurosurg Psychiatry 77(9): 1036-9) and generally lower amount of distinct white matter lesions (i.e. plaques) in the brain and less evidence for brain inflammatory activity (Lucchinetti, C. and W. Bruck (2004). The pathology of primary progressive multiple sclerosis. Mult Scler 10 Suppl 1: S23-30) and, most importantly, PP-MS patients do not respond to immunomodulatory therapies with proven efficacy in RRMS (Leary, S. M. and A. J. Thompson (2005). Primary progressive multiple sclerosis: current and future treatment options. CNS Drugs 19(5): 369-76).

Both new imaging modalities and pathological data suggest that in PP-MS, CNS pathology is more diffuse (Filippi, M., M. A. Rocca, et al. (2002). Correlations between structural CNS damage and functional MRI changes in primary progressive MS. Neuroimage 15(3): 537-46; Rovaris, M., E. Judica, et al. (2008). Large-scale, multicentre, quantitative MRI study of brain and cord damage in primary progressive multiple sclerosis. Mult Scler. 14(4): 455-64) and occurs to some extent independently of focal lesions (Sastre-Garriga, J., G. T. Ingle, et al. (2004). Grey and white matter atrophy in early clinical stages of primary progressive multiple sclerosis. Neuroimage 22(1): 353-9.; Kutzelnigg, A., C. F. Lucchinetti, et al. (2005). Cortical demyelination and diffuse white matter injury in multiple sclerosis. Brain 128 (Pt 11): 2705-12; Rovaris, M., A. Gallo, et al. (2005). Axonal injury and overall tissue loss are not related in primary progressive multiple sclerosis. Arch Neurol 62(6): 898-902).

The cervical spinal cord is the major target of the disease process in PP-MS, underlying most of the clinical disability. The diffuse CNS process in PP-MS is characterized by microglial activation and diffuse axonal injury in the white matter and by cortical demyelination and neuronal loss in the gray matter. Additionally, low level but persistent endothelial abnormalities and blood-brain-barrier (BBB) leak, both in normal appearing white and gray matter have been observed.

There are currently no treatments with proven therapeutic efficacy for PP-MS (Leary, S. M. and A. J. Thompson (2005). Primary progressive multiple sclerosis: current and future treatment options. CNS Drugs 19(5): 369-76). Neither interferon-beta preparations (Leary, S. M., D. H. Miller, et al. (2003). Interferon beta-1a in primary progressive MS: an exploratory, randomized, controlled trial. Neurology 60(1): 44-51; Montalban, X. (2004). Overview of European pilot study of interferon beta-1b in primary progressive multiple sclerosis. Mult Scler 10 Suppl 1: S62; discussion 62-4) nor glatiramer acetate (Wolinsky, J. S., P. A. Narayana, et al. (2007). Glatiramer acetate in primary progressive multiple sclerosis: results of a multinational, multicenter, double-blind, placebo-controlled trial. Ann Neurol 61(1): 14-24) could slow down the accumulation of disability in PP-MS. Several Phase II trials of Mitoxantrone in PP-MS were initiated, but none reported positive effect. A recently reported large multicentric, placebo-controlled Phase II trial of Rituximab in PP-MS also failed to demonstrate any effect on the accumulation of disability in this patient population (see http://www.nationalmssociety.org/news/news-detail/index.aspx?nid=221.)

These data collectively indicate that therapies targeting the immune system and specifically the formation of Gd-enhancing MS lesions do not demonstrate beneficial effect in PP- MS. In agreement with the reviewed hypothesis that the pathophysiology of PP-MS may rely more on neurodegenerative, rather than immune-mediated mechanisms of CNS tissue destruction, a pilot trial of the neuroprotective agent riluzole showed a mild effect on inhibiting the development of cervical cord atrophy in the PP-MS cohort (Kalkers, N. F., F. Barkhof, et al. (2002). The effect of the neuroprotective agent riluzole on MRI parameters in primary progressive multiple sclerosis: a pilot study. Mult Scler 8(6): 532-3) which however, did not reach statistical significance.

In another study (A. Bosco, G. Cazzato, et al., Nuova Rivista di Neurologia, 7 (1997), 90-94) with patients suffering from the chronic-progressive form of MS, which is clinically distinct from PP-MS, idebenone (at a dose of 90 mg/day) given in combination with methylprednisolone over 240 days could not be shown to have any clinical or neurophysiological efficacy.

Accordingly, there is a strong need in the art to provide further means for treating and/or preventing several symptoms associated with of primary progressive Multiple Sclerosis.

Said object is achieved by providing Idebenone for preparing a medicament for curative treating or preventing of primary progressive Multiple Sclerosis.

DESCRIPTION OF THE INVENTION

Specifically, the invention relates to the administration of Idebenone (2,3-dimethoxy-5-methyl-6-(10-hydroxydecyl)-1,4-benzoquinone) to patients with PP-MS.

This is surprising since it has been reported previously that Idebenone can be used for the treatment of hypertrophic cardiomyopathy associated with Friedreich's Ataxia (FRDA; U.S. Pat. No. 6,133,322; Rustin, 1999) or dilated cardiomyopathy observed in DMD, BMD and XLDCM-patients (WO2006/100017).

However, the use of Idebenone in the treatment of PP-MS had never been contemplated before.

Unlike RRMS for which a number of medications are approved and used in daily clinical practice no treatment has been proven to modify the course of PP-MS and therefore PP-MS constitutes a severe disease with high medical need.

Idebenone of the present invention surprisingly provide a new effective and safe treatment of PP-MS. Idebenone according to the present invention attenuate symptoms of PP-MS, attenuate, retard, cure, prevent, and/or inhibit neurodegeneration and/or CNS tissue destruction in PP-MS patients.

Additionally, Idebenone according to the present invention represent a therapy with extensive safety and tolerability data.

A first aspect of the present invention relates to the use of Idebenone for the preparation of a medicament for treating or preventing PP-MS.

In this aspect also a method of treating or preventing PP-MS by administering a sufficient amount of Idebenone is contemplated.

"Treating" or "treatment" of a disease, such as PP-MS, encompass the curative treatment of the disease, the treatment of one or more symptoms of the disease, the curative treatment of one or more malfunctions or one or more destructions associated with the disease or the elimination or alleviation of symptoms or pain associated with the disease. In PP-MS "treating" or "treatment" preferably refer to the curative treatment, attenuation or elimination of neurodegeneration and/or CNS tissue destruction.

"Preventing" or "prevention" of a disease, such as PP-MS, encompass the retardation, retardation of the onset or the inhibition of the disease or the retardation, retardation of the onset or the inhibition of one or more symptoms, one or more malfunctions or of one or more destructions associated with the disease, or the inhibition of symptoms or pain associated with the disease. In PP-MS "preventing" or "prevention" preferably refer to the prevention or inhibition of neurodegeneration or CNS tissue destruction in patients.

In preferred embodiments Idebenone is to be administered orally in a dosage from 5 mg/kg body weight/day to 60 mg/kg/day, more preferably from 10 mg/kg/day to 60 mg/kg/day, and most preferred from 30 mg/kg/day to 50 mg/kg/day.

Preferred doses for oral administration are between 450 mg/day to 2250 mg/day, more preferred are doses of 900 mg/day to 2250 mg/day.

In one embodiment, oral administration of idebenone is in a form of a tablet.

In other embodiments of this invention the mode of administration of Idebenone is selected from oral, i.p., i.v., i.m., i.c., parenteral, intranasal, transmucosal, sublingual and transdermal.

In a preferred embodiment idebenone is administered via transmucosal administration. Preferred doses for transmucosal administration range from 0.01 mg/kg/day to 60 mg/kg/day, more preferable from 0.01 mg/kg/day to 20 mg/kg/day.

In one embodiment, transmucosal administration of idebenone is in the form of a suppository, drop, chewing gum, fast dissolving tablet or spray.

In further embodiments Idebenone is to be administered one or more times daily over at least 3 months, preferably over at least 6 months, more preferably for about 6 to about 12 months, most preferably lifelong after disease onset.

In another embodiment, Idebenone is to be administered in combination with a second therapeutic agent.

Idebenone may be administered simultaneously, subsequently or previously as compared to the second therapeutic agent. Idebenone may also be administered in the same or in a different time schedule compared to the second therapeutic agent. Idebenone may also be administered in the same or a different route of administration compared to the second therapeutic agent. Preferably, Idebenone is administered orally or transmucosally and the second therapeutic agent is administered oral or i.v, i.p., i.m., i.c.

The second therapeutic agent may be selected from Methylprednisolone, a Corticosteroid, an Interferon, Glatiramer acetate Mitoxantrone, Rituximab, Daclizumab and Natalizumab.

Preferably, the second therapeutic agent is selected from Methylprednisolone and Rituximab.

More preferably, Idebenone is not administered together with Methylprednisolone as in the therapy regime applied in a clinical study (A. Bosco, G. Cazzato, et al., Nuova Rivista di Neurologia, 7 (1997), 90-94). Even more preferably, orally administered Idebenone of less than 200 mg/day is not employed together with Methylprednisolone i.v.

Still more preferably, orally administered Idebenone of less than 100 mg/day is not employed together with Methylprednisolone i.v.

In a second aspect of the present invention pharmaceutical preparations are provided, such as a kit, a combination of agents or a pharmaceutical composition.

In one embodiment, a kit comprising a) Idebenone and b) an agent selected from Methylprednisolone, a Corticosteroid, an Interferon, Glatiramer acetate Mitoxantrone, Rituximab, Daclizumab or Natalizumab is contemplated.

In another embodiment, a Combination of a) Idebenone together with b) Methylprednisolone, a Corticosteroid, an Interferon, Glatiramer acetate Mitoxantrone, Rituximab or Natalizumab is provided.

In still another embodiment, a Pharmaceutical Composition comprising a) Idebenone together with b) Methylprednisolone, a Corticosteroid, an Interferon, Glatiramer acetate Mitoxantrone, Rituximab, Daclizumab or Natalizumab is provided.

One year of pre-treatment baseline will be followed by 1:1 randomization to placebo and Idebenone 750 mg tid (2250 mg daily dose) for 2 years. All outcome measures will be collected every 6-12 months as indicated.

Figure 1:
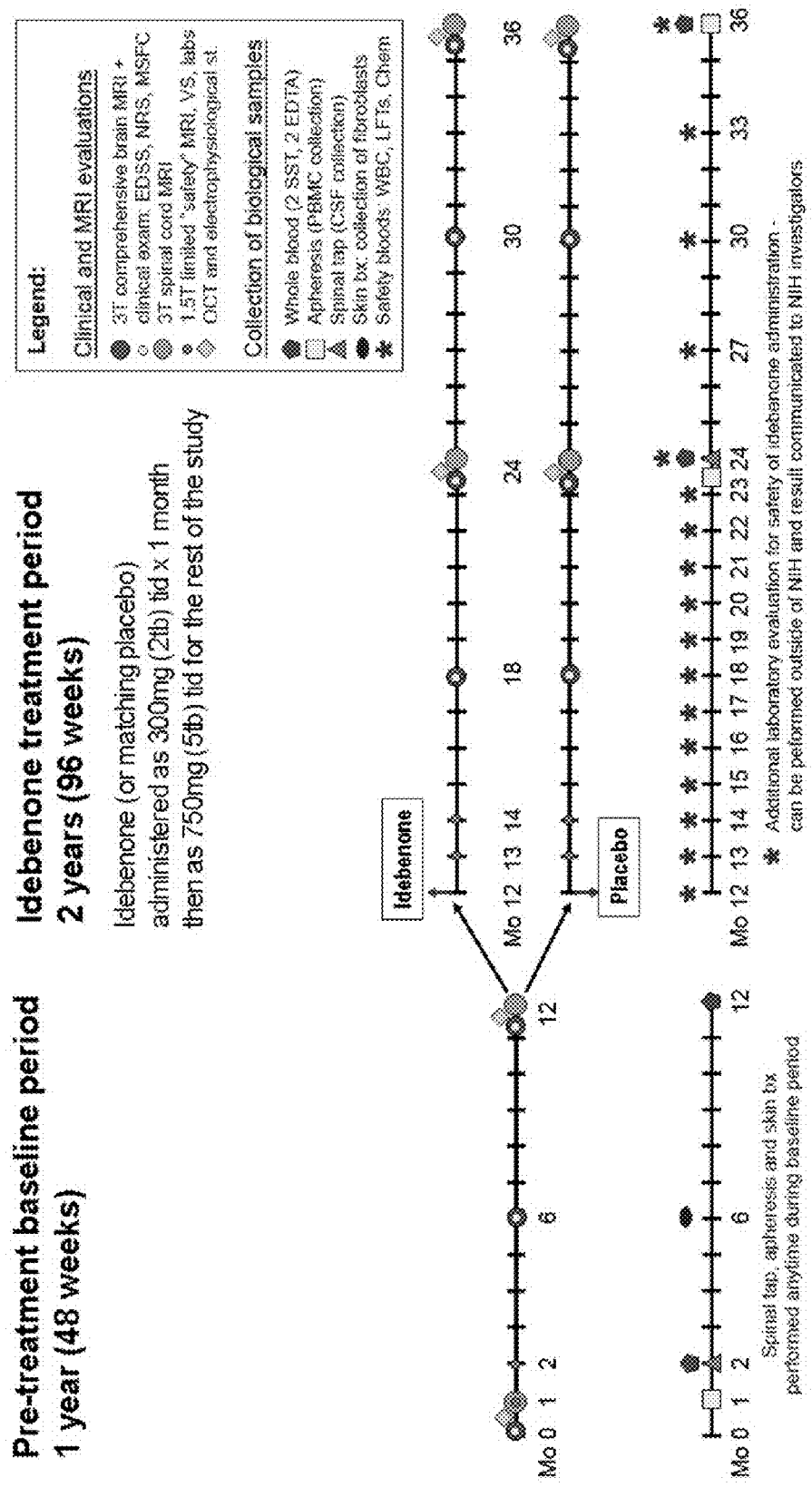
FIG. 1: Idebenone in PP-MS Clinical Trial Design
Figure 2:
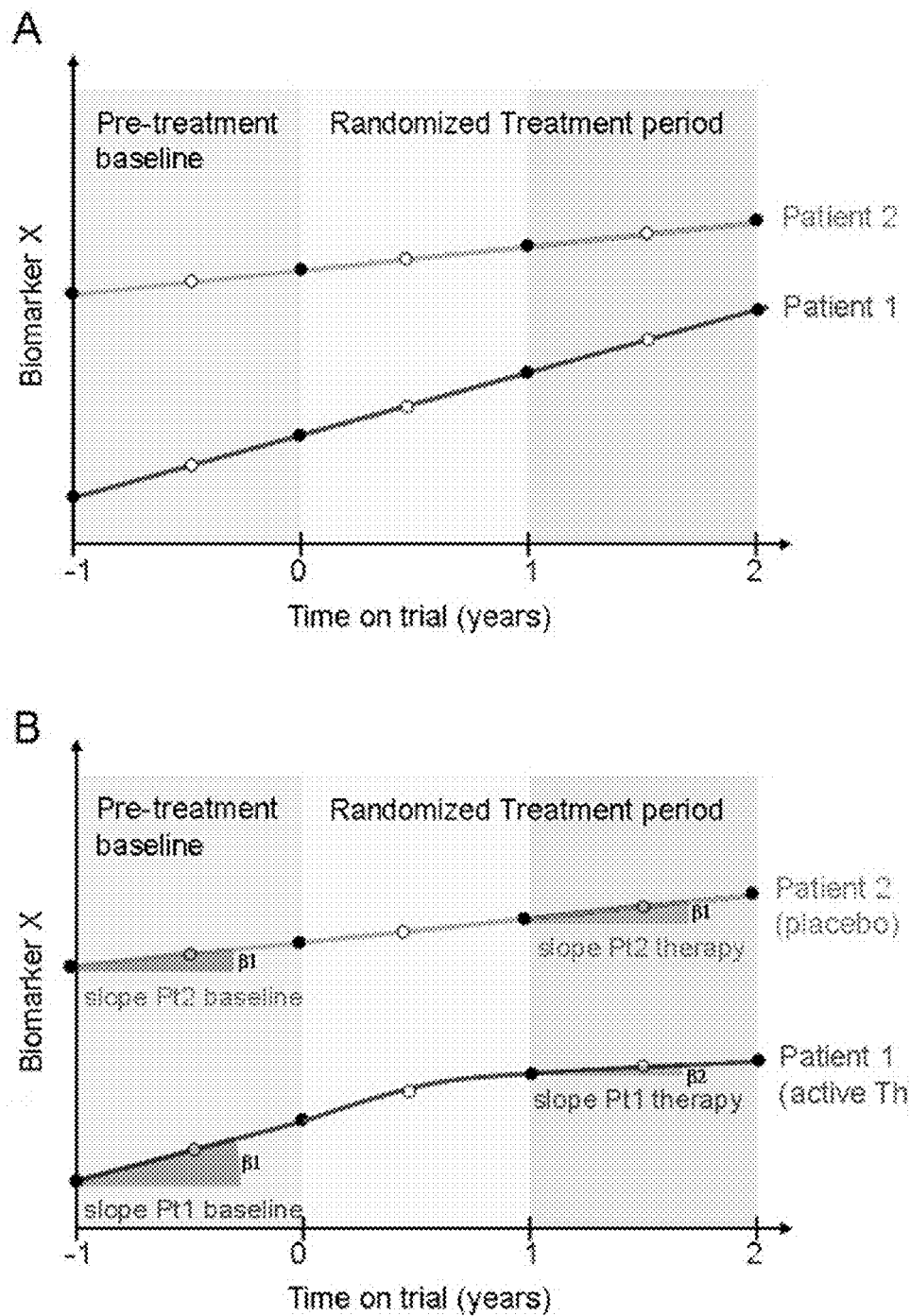

FIG. 2: Efficacy measures adjusted for individualized rates of development of CNS tissue destruction in PP-MS A) Current trial is based on three assumptions, which are supported by the literature (Ingle, G. T., V. L. Stevenson, et al. (2003). Primary progressive multiple sclerosis: a 5-year clinical and MR study. Brain 126 (Pt 11): 2528-36):
1. The slopes of CNS tissue destruction are linear for the majority of PP-MS patients. Therefore, the collection of 2-3 time-points for each biomarker during the baseline period will allow estimation of the individual slopes of CNS tissue destruction
2. The slopes of CNS tissue destruction differ among individual PP-MS patients
3. The cross-sectional data (i.e. single, initial measurement of the biomarker) do not predict the slope/rate of CNS tissue destruction B) Current trial and proposed analyses use the assumptions indicated above in order to increase the statistical power: for each patient, the area under curve (AUC) will be calculated for those biomarkers measured every 6 months and the AUC during the baseline period will be compared to the AUC during the second year of treatment in order to calculate the difference between these two measures. These individualized differences will be then compared on a group level between active treatment and placebo arms. For biomarkers collected every 12 months, the average of 2 baseline time-points (year −1 and 0) will be compared to the average of 2 therapy time-points (year 1 and 2) in an analogous manner.

DETAILED DESCRIPTION OF THE INVENTION

Idebenone

Idebenone is a synthetic analogue of coenzyme Q10 (CoQ10), the vital cell membrane antioxidant and essential constituent of the adenosine-triphosphate (ATP)-producing mitochondrial electron transport chain (ETC). Idebenone has the ability to operate under low oxygen tension situations. Due to its ability to inhibit lipid peroxidation, Idebenone protects cell membranes and mitochondria from oxidative damage (Zs.-Nagy I (1990) Chemistry, toxicology, pharmacology and pharmacokinetics of Idebenone: a review. Arch. Gerontol. Geriatr. 11:177-186). Its antioxidant properties protect against cerebral ischemia and nerve damage in the central nervous system. Idebenone also interacts with the ETC, preserving ATP formation in ischemic states. This compound is already used as a nootropic drug and has also been shown to stimulate nerve growth factor, a characteristic that could be important in the treatment of Alzheimer's and other neurodegenerative diseases. Idebenone is described in the specification of Japanese Patent Examined Publication No. 3134/1987 filed by Takeda Chemical Industries, Ltd.

Idebenone has the following formula:

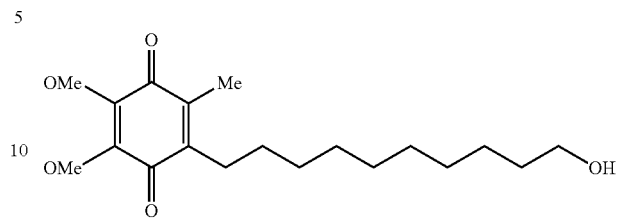

Formula 1: 2,3-dimethoxy-5-methyl-6-(10-hydroxy-decyl)-1,4-benzoquinone, Idebenone Idebenone is safe and well tolerated which means that it can be used as a pharmaceutical active agent in a medicament.

In one embodiment, Idebenone of the present invention are in a crystalline form, in a powder form, in a gelatin capsule, formulated as tablets, formulated as chewable tablets, formulated in a solution or formulated in an oromucosal, transmucosal or sublingual preparation.

Modes of Administration of Idebenone

Preferred modes of administration for Idebenone are oral, i.p., i.v., i.m., Lc, parenteral, intranasal, transdermal, and transmucosal whereas the oral and transmucosal administrations are the most preferred modes of administration.

In one embodiment of the present invention, Idebenone is administered orally in a daily dosage of ranges from 450 mg/day to 2250 mg/day, more preferably 900 mg/day to 2250 mg/day.

In one embodiment, Idebenone is administered orally in a daily dosage per kg body weight of a patient, which is from 5 mg/kg/day to 60 mg/kg/day, more preferably in a dosage range of 10 mg/kg/day to 60 mg/kg/day and most preferred in a dosage range of 30 mg/kg/day to 50 mg/kg/day.

In one embodiment oral administration is in the form of a tablet.

In another embodiment of the present invention, idebenone is administered via the transmucosal route.

Preferred doses for transmucosal administration range from 0.01 mg/kg/d to 60 mg/kg/d, more preferably from 0.01 mg/kg/d to 20 mg/kg/day.

In one embodiment, transmucosal administration of idebenone is in the form of a suppository, drop, chewing gum, fast dissolving tablet or spray.

In another embodiment, Idebenone is to be administered one or more times daily over at least 1 week, preferably over at least 3 weeks, preferably over at least 1 month, preferably over at least 2 month, preferably over at least 3 months, preferably over at least 6 months, preferably for about 6 to about 12 months, most preferably lifelong after disease onset.

Any suitable route of administration for Idebenone may be employed for providing a mammal, especially a human with an effective dosage of Idebenone. Further modes of administration include rectal, topical, ocular, pulmonary or nasal administration. The dosage forms include, e.g., tablets, troches, dispersions, suspensions, solutions, capsules, creams, ointments and aerosols, whereas tablets or fast dissolving tablets are most preferred.

The effective dosage of the active ingredient employed may vary depending on the particular compounds employed, the mode of administration, the condition being treated and the severity of the condition being treated. Such dosage may be ascertained readily by a person skilled in the art, a preferred dosage having been mentioned above. Idebenone as used in the context of the present invention is preferably formulated into a dosage form prior to administration. Accordingly, Idebenone or the variant thereof may be combined with any suitable pharmaceutical carrier. The pharmaceutical preparations for use in accordance with the present invention may be prepared by normal procedures using well-known and readily available ingredients. In making the formulations, Idebenone is usually mixed with a carrier, or diluted by a carrier, or enclosed with a carrier, which may be in the form of a capsule, cachet, paper or other container. When the carrier serves as a diluent, it may be a solid, semi-solid, or liquid material, which acts as a vehicle, excipient or medium for the active ingredient. The compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions, sterile packaged powders, suppositories, drops, chewing gums, fast dissolving tablets or sprays.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents and/or flavoring agents. The compositions of the invention may be formulated so as to provide quick, sustained or delayed release of the active ingredient after administration to the patient.

Idebenone can be combined with excipients, fillers, solvents, diluents, dyes and/or binders. The choice of auxiliary substances as well as the amounts thereof to be used depends on whether the medicinal drug is to be administered orally, transmucosally intravenously, intraperitoneally, intradermally, intramuscularly, intranasally, buccally or topically. For oral application suitable preparations are in the form of tablets, sugar-coated pills, capsules, granular powders, drops, juices and syrups, while for parenteral, topical and inhalative application suitable forms are solutions, suspensions, easily reconstitutable dry preparations as well as sprays. Idebenone can be administered in a sustained-release substance, in dissolved form or in a plaster, optionally with the addition of agents promoting penetration of the skin, and are suitable as percutaneous application preparations. Forms of preparations that can be used orally or percutaneously may produce a delayed release of the compounds. Idebenone formulations are e.g. described in several patents of Takeda such as for example WO9907355 and JP11116470. Other preferred Idebenone formulations, in particular trans-mucosal formulations, are described in WO 2008/019769.

Preferred oral formulations for use in accordance with the present invention contain 150 mg of Idebenone in a film-coated tablet containing lactose monohydrate, microcrystalline cellulose, croscarmellose sodium povidone, magnesium stearate, silicon dioxide.

In a further preferred embodiment, Idebenone may be administered in combination with a second therapeutic agent, wherein said second therapeutic agent is preferably selected from Methylprednisolone, one or more Corticosteroids, one or more Interferons, e.g. Interferon beta-1a (trade names Avonex, CinnoVex, ReciGen and Rebif) or one of Interferon beta-1b (U.S. trade name Betaseron, in Europe and Japan Betaferon), Glatiramer acetate (Copaxone), Mitoxantrone, Rituximab, Daclizumab or Natalizumab.

Idebenone and the further active agent can be used simultaneously, separately or sequentially in order to treat or prevent the disease symptoms. The two active agents may be provided in a single dosage form or a separate formulation, each formulation containing at least one of the two active agents. One or both of the two active agents may be formulated as a bolus.

EXAMPLES

The following examples further illustrate the present invention.

Example 1

General Aspects of a Clinical Study Design to Assess the Efficacy of idebenone in PP-MS Without being bound to any theory by reducing oxidative stress and improving mitochondrial respiratory chain function, idebenone has a therapeutic effect in patients with PP-MS. Efficacy of idebenone in PP-MS can be determined in a clinical study using an adaptive trial design. Said study design starts with a 12 month pre-treatment baseline period, where magnetic resonance imaging (MRI), clinical and biomarker measurements will be collected which is to be followed with a randomized, double blind placebo controlled period of 24 months in which efficacy of idebenone is compared to placebo.

This trial design allows:
1) To obtain longitudinal quantitative MRI, clinical and electrophysiological data in untreated PP-MS patients before randomization that will be utilized for the selection of the most sensitive primary outcome measure.
2) To obtain patient-specific pre-randomization baseline for all collected outcome measures, which is expected to increase the statistical power of randomized studies with continuous outcome measures (Murray, G. D., D. Barer, et al. (2005). Design and analysis of phase III trials with ordered outcome scales: the concept of the sliding dichotomy. J Neurotrauma 22(5): 511-7; Young, F. B., K. R. Lees, et al. (2005). Improving trial power through use of prognosis-adjusted end points. Stroke 36(3): 597-601; Frost, C., M. G. Kenward, et al. (2008). Optimizing the design of clinical trials where the outcome is a rate. Can estimating a baseline rate in a run-in period increase efficiency? Stat Med 27(19): 3717-31). Based on published longitudinal studies using analogous, but presumably less sensitive biomarkers of CNS tissue destruction (e.g. ventricular atrophy, cross-sectional cervical spinal cord atrophy collected at 1.5 T MRI (Ingle, G. T., V. L. Stevenson, et al. (2003). Primary progressive multiple sclerosis: a 5-year clinical and MR study. Brain 126(Pt 11): 2528-36) two assumptions are made (FIG. 2A): (i) CNS tissue destruction develops in a linear manner within a 3-5 year time-frame in the majority of PP-MS patients, and (ii) the slopes of the linear development of CNS tissue destruction differ among individual patients. Based on these two assumptions, this trial design will allow adjustment for the individualized rates of development of CNS tissue destruction (FIG. 2B), which is expected to increase the power to detect treatment relevant differences between placebo and idebenone therapy groups (Murray, G. D., D. Barer, et al. (2005). Design and analysis of phase III trials with ordered outcome scales: the concept of the sliding dichotomy. J Neurotrauma 22(5): 511-7; Young, F. B., K. R. Lees, et al. (2005). Improving trial power through use of prognosis-adjusted end points. Stroke 36(3): 597-601; Frost, C., M. G. Kenward, et al. (2008). Optimizing the design of clinical trials where the outcome is a rate. Can estimating a baseline rate in a run-in period increase efficiency? Stat Med 27(19): 3717-31).

In the randomized part of the study idebenone at a dose of 2250 mg/day (5×150 mg tablets three times per day) will be compared to placebo.

Because PP-MS is usually diagnosed in the early/late forties, and to allow for sensitive detection of any therapeutic efficacy the upper age limit of patients in this trial will be 55 years. This age limit will minimize the contribution of aging to the development of CNS atrophy and will ensure that aging will not limit CNS repair mechanisms.

Example 2

Clinical Study to Assess the Efficacy of Idebenone in PP-MS

Patients:

The study population consists of 66 patients (33 per arm) with clinically definite PP-MS; age 18-55 (inclusive) with disability ranging from none to moderately severe (EDSS 0-7, inclusive). Children will be excluded, because a diagnosis of PP-MS is virtually nonexistent in children, and the age of the participants will be limited to 55 years, because of evidence that remyelination and repair strategies may be ineffective in older patients.

Inclusion Criteria Include:
1. PP-MS as determined by the 2005 modification of McDonald's diagnostic criteria (Polman, C. H., S. C. Reingold, et al. (2005). Diagnostic criteria for multiple sclerosis: 2005 revisions to the "McDonald Criteria". Ann Neurol 58(6): 840-846).
2. Age from 18-55 years (inclusive)
3. EDSS measure of neurological disability from 1 (no disability, clinical signs only) to 7 (ambulatory with bilateral support) (Kurtzke, J. F. (1983). Rating neurologic impairment in multiple sclerosis: an expanded disability status scale (EDSS). Neurology 33(11): 1444-52).
4. Able to provide informed consent
5. Willing to participate in all aspects of trial design and follow-up
6. Not receiving any immunomodulatory/immunosuppressive therapies for a period of at least 3 months before enrollment in the study Exclusion Criteria Include:
1. Alternative diagnoses that can explain neurological disability and MRI findings
2. Clinically significant medical disorders that, in the judgment of the investigators could cause CNS tissue damage or limit its repair, or might expose the patient to undue risk of harm or prevent the patient from completing the study
3. Abnormal screening/baseline blood tests
4. Patients who are receiving any immunosuppressive therapies (including cytostatic agents) due to the concern that these drugs may contribute to neurodegeneration or limit CNS repair Study Conduct:

General

Based on current sample size estimates up to 80 PP-MS are to be screened to yield at least 66 patients that will finish the treatment phase of the study. Patients are randomized 1:1 to receive either active therapy (Idebenone 750 mg po tid; daily dose of 2250 mg, given as tablets with a dose strength of 150 mg) or placebo. The treatment phase of the trial is preceded by a 1 year pre-treatment baseline period, which will serve a dual purpose: (i) to collect individualized data on biomarkers of CNS tissue damage, and (ii) to use these longitudinal data for the selection of the primary outcome measure and for more precise sample size estimates.

All eligible patients undergo combined neurological, neuroimaging and research biomarker/immunological evaluations for 12 months (44 weeks) during the baseline period. The complete evaluation requires a total of 6 outpatient visits in 44 weeks.

Patients who complete 12 months of baseline are to be randomized to active treatment or placebo by block stratification using a single condition: Age (age<50 and age≧50). Because epidemiological data indicate that age is a major determinant of the efficiency of CNS repair this randomization strategy ensures that both placebo and idebenone treatment groups are comparable in this respect.

After randomization, patients are to be followed during 9 outpatient visits by combined neurological, neuroimaging and research biomarker/immunological evaluations for an additional 24 months.

Efficacy Evaluations:

A) Clinical and Functional Evaluations to be Performed Every 6 Months
1. Comprehensive neurological evaluation
2. Expanded Disability Status Scale (EDSS)
3. Scripps Neurological Rating Scale (NRS) (Sharrack, B. and R. A. Hughes (1996). Clinical scales for multiple sclerosis. J Neurol Sci 135(1): 1-9).
4. MS Functional Composite Scale (MSFC) (Cutter, G. R., M. L. Baier, et al. (1999). Development of a multiple sclerosis functional composite as a clinical trial outcome measure. Brain 122 (Pt 5): 871-82), which consists of 3 functional tests:
   a. Paced Auditory Single Digit Addition Test (PASAT)—measure of cognitive skills
   b. Timed 25 foot walk—measure of ambulation
   c. 9-hole peg test—measure of fine finger motor movements
5. Visual Analogue Scale (VAS)
6. Symbol Digit Modality Test (Sepulcre, J., S. Vanotti, et al. (2006). Cognitive impairment in patients with multiple sclerosis using the Brief Repeatable Battery-Neuropsychology test. Mult Scler 12(2): 187-95).

B) Neuroimaging Evaluation:
MRI imaging will consist of:
1) 3 T MRI of the brain, which is performed every 6 months. This MRI focuses on volumetric analyses (i.e. whole brain atrophy, white matter and gray matter atrophy, cortical mantle thickness); evaluation of brain structural integrity by means of quantitative magnetization transfer ratios (MTR), magnetic resonance spectroscopy (MRS) and T1 relaxation time. Because inflammatory activity is much less prominent in PP-MS as compared to RRMS and consequently, the vast majority of PP-MS patients do not have evidence of gross blood-brain barrier (BBB) disruption as measured by contrast-enhancing lesions (CEL), gadolinium (Gd) administration to the 3 T MRI scans is to be limited and performed at baseline (Weeks 0 and 44) and then repeated after their 1$^{st}$ (week 96) and 2$^{nd}$ (week 140) years of therapy.

2) 3 T MRI of the spinal cord with focus on volumetric analysis of cervical spinal cord atrophy and the feasibility and value of spinal cord structural integrity measures, such as T1 relaxation time and MTR. This scan is performed every 12 months and will not include Gd administration.

3) Series of 3 monthly limited 1.5 T MRIs of the brain. The series of 3 monthly MRIs is performed only twice during the study duration: at the screening and at the initiation of the treatment phase. Because PP-MS patients have a paucity of BBB disruption measured by CEL, the series of 3 monthly MRIs at the initiation of treatment is used in this trial only as a safety measure: to ensure that Idebenone is not inducing immune activation that would result in the increase of CEL upon initiation of therapy phase as compared to pre-treatment baseline.

C) Optical Coherence Tomography (OCT) is Performed Every 12 Months.

OCT is a new noninvasive high-resolution method that measures the retinal nerve fiber layer (RNFL) thickness. It works by measuring the echo time delay and intensity of back-reflection of light from different structures in the eye. Recent studies have shown that OCT can detect RNFL thinning, possibly due to axon degeneration, within the retinas of patients with MS, regardless of a clinical history of optic neuritis (Kaltenbach, K. and J. Frederiksen (2007). Optical coherence tomography in optic neuritis and multiple sclerosis: a review. Eur J Neurol 14(8): 841-9). Moreover, RNFL thickness appears associated with global brain atrophy, (manifested by increasing CSF volume) (Gordon-Lipkin, E., B. Chodkowski, et al. (2007). Retinal nerve fiber layer is associated with brain atrophy in multiple sclerosis. Neurology 69(16): 1603-9).

D) Transcranial Magnetic Stimulation (TMS) and Central Motor Conduction Time (CMCT) Calculation is Performed Every 12 months.

Neurophysiological testing can assess the intactness of conduction through the long tracts, such as the corticospinal tract (CST). Because CST is invariably affected in PP-MS, the use of motor evoked potentials (MEP) as a quantifiable measure of corticospinal function is examined as a potential new outcome measure. TMS is a non-invasive technique for evaluating the function of central motor pathways. Single pulse TMS is used to determine the motor evoked potential (MEP), the response generated by excitation of cortical neurons and recorded at the target muscle, and is used to calculate the central motor conduction time (CMCT). In MS patients, CNS dysfunction manifests itself in the form of slowed conduction through demyelinated portions of the corticospinal tracts or more severe disruption of conduction as a result of axonal loss or severe demyelination. This results in a prolongation of CMCT or dispersion of the MEP response such as in a conduction block with resultant decrease in MEP amplitude (Hess, C. W., K. R. Mills, et al. (1987). Magnetic brain stimulation: central motor conduction studies in multiple sclerosis. Ann Neurol 22(6): 744-52; Schriefer, T. N., C. W. Hess, et al. (1989). Central motor conduction studies in motor neurone disease using magnetic brain stimulation. Electroencephalogr Clin Neurophysiol 74(6): 431-7).

Outcome Measures

The following outcome measures are useful in determining the efficacy of idebenone in PP-MS:

Inhibition of development of brain atrophy: comparison of individualized rates of progression of brain atrophy between Idebenone and placebo Inhibition of individualized rates of development of brain atrophy: effect of Idebenone versus placebo on individualized rates of development of brain atrophy Inhibition of development of brain gray matter atrophy: comparison between Idebenone and placebo of segmented gray matter atrophy progression Inhibition of individualized rates of development of brain gray matter atrophy: effect of Idebenone versus placebo on individualized rates of development of segmented gray matter atrophy Inhibition of enlargement of ventricular volume: comparison between Idebenone and placebo of segmented volume of 3$^{rd}$ ventricle Inhibition of individualized rates of enlargement of ventricular volume: effect of Idebenone versus placebo on individualized rates of enlargement of segmented volume of 3$^{rd}$ ventricle Inhibition of development of cervical spinal cord (SC) atrophy: comparison between Idebenone and placebo of SC atrophy progression Inhibition of individualized rates of development of cervical SC atrophy: effect of Idebenone versus placebo on individualized rates of development of SC atrophy Inhibition of neuroaxonal destruction as assessed by NAA/Cr ratio on slab MRS (ROI in normal appearing white matter and in deep gray matter): comparison of progression of NAA loss (as detected by NAA/Cr ratio) between Idebenone and placebo Inhibition of individualized rates of neuroaxonal destruction as assessed by NAA/Cr ratio on slab MRS(ROI in normal appearing white matter and in deep gray matter): effect of Idebenone versus placebo on individualized rates of neuroaxonal destruction Inhibition of neuroaxonal destruction as assessed by T1 relaxation time in the brain (ROI in normal appearing white matter and in deep gray matter): comparison between Idebenone and placebo Inhibition of individualized rates of neuroaxonal destruction as assessed by T1 relaxation time in the brain (ROI in normal appearing white matter and in deep gray matter): effect of Idebenone versus placebo on individualized rates of neuroaxonal destruction Inhibition of neuroaxonal destruction as assessed by T1 relaxation time in the cervical spinal cord: comparison between Idebenone and placebo Inhibition of individualized rates of neuroaxonal destruction as assessed by T1 relaxation time in the cervical spinal cord: effect of Idebenone versus placebo on individualized rates of neuroaxonal destruction Inhibition of neuroaxonal destruction as assessed by Magnetization Transfer Ratio (MTR) in the brain (ROI in normal appearing white matter and in deep gray matter): comparing between Idebenone and placebo Inhibition of individualized rates of neuroaxonal destruction as assessed by Magnetization Transfer Ratio (MTR) in the brain (ROI in normal appearing white matter and in deep gray matter): effect of Idebenone versus placebo on individualized rates of neuroaxonal destruction Inhibition of changes in axonal integrity as assessed by axial diffusivity and of changes in myelin integrity as assessed by radial diffusivity on brain DTI imaging: comparison between Idebenone and placebo Inhibition of individualized changes in axonal integrity as assessed by axial diffusivity and of changes in myelin integrity as assessed by radial diffusivity on brain DTI imaging: effect of Idebenone versus placebo on individualized rates of neuroaxonal destruction Progression of lower extremity disability as assessed by 25 foot walk component of MSFC comparing Idebenone to placebo Progression of upper extremity/fine motor movements disability as assessed by 9 hole peg test component of MSFC comparing Idebenone to placebo Progression of neurological disability as assessed by MSFC comparing Idebenone to placebo Progression of neurological disability as assessed by Scripps NRS AUC comparing Idebenone to placebo Progression of neurological disability as assessed by EDSS AUC comparing Idebenone to placebo Prolongation of CMCT as assessed by TMS (comparing Idebenone to placebo and comparing inhibitory effects of Idebenone versus placebo on individualized rates of CMCT prolongation)

Progression in cognitive dysfunction as assessed by PASAT component of MSFC AUC comparing Idebenone to placebo Progression in cognitive dysfunction as assessed by Symbol Digit Modality Test AUC comparing Idebenone to placebo Statistical Analyses of Outcome Measures 1. Differences in the collected neuroimaging, clinical and biological data are compared between placebo and Idebenone cohorts at the end of the 2 year treatment period by non-parametric Rank Sum test, or, if permitted, by parametric t-test for each outcome measure.
2. In order to increase statistical power by employing individualized rates of disease progression as determined from 1 year of pre-treatment baseline period, in a second type of analysis individualized changes in quantifiable parameters are analyzed by comparing data obtained during the pre-treatment baseline period to data obtained during therapy (FIG. 2B). statistical analyses are performed comparing these individualized changes between placebo and Idebenone subgroups as outlined below:
    a. For data collected only at 2 time-points (i.e. single collection during pre-treatment baseline and single collection at 1 year of therapy), for each individual the %-change between baseline and therapy time-points are calculated
    b. For data collected at 4 time-points (i.e. twice during pre-treatment baseline and twice during therapy phase) for each individual % change between average of 2 baseline samples and average of 2 therapy samples is to be calculated. In previous studies it was determined that this process greatly increases statistical power by limiting biological noise (Bielekova, B., M. Catalfamo, et al. (2006). Regulatory CD56bright natural killer cells mediate immunomodulatory effects of IL-2Ralpha-targeted therapy (daclizumab) in multiple sclerosis. PNAS 103(15): 5941-5946).
    c. For data collected every 6 months (i.e. clinical data and quantitative brain MRI data) the area under curve (AUC) for 3 data points obtained during pre-treatment baseline period (weeks 0-44) is to be calculated and compared to AUC for 3 data points obtained during the second year of therapy (weeks 92-140; FIG. 2B).

Differences between placebo and Idebenone subgroups for each of these newly derived parameters are analyzed by utilizing non-parametric Rank Sum test, or, if permitted, by parametric t-test. We will use P value of 0.05 as determinant of statistical significance.

The invention claimed is:

1. A method for treating primary progressive multiple sclerosis (PP-MS) which method comprises administering Idebenone to a patient to treat PP-MS in the patient.

2. The method of claim 1, wherein the Idebenone is administered by oral administration in a dosage of from 5 mg/kg/day to 60 mg/kg/day.

3. The method of claim 1, wherein Idebenone is administered by oral administration in a dosage of 450-2250 mg/day.

4. The method of claim 1, wherein the Idebenone is administered by transmucosal administration in a dosage of 0.01 mg/kg/day to 60 mg/kg/day.

5. The method of claim 1, wherein the Idebenone is administered one or more times daily over at least 3 months, after onset of PP-MS in the patient.

6. The method of claim 1, wherein the mode of administration of Idebenone is selected from the group consisting of oral, i.p., i.v., i.m., i.c., parenteral, intranasal, transdermal and transmucosal.

7. The method of claim 1, wherein the Idebenone is administered in a form of a tablet, suppository, drop, chewing gum, fast dissolving tablet or spray.

8. The method of claim 1, wherein the Idebenone is administered in combination with a second therapeutic agent.

9. The method of claim 1, wherein the Idebenone is administered to a patient having PP-MS, thereby treating PP-MS in the patient.

10. The method of claim 9, wherein the Idebenone is administered by oral administration in a dosage from 5 mg/kg/day to 60 mg/kg/day.

11. The method of claim 6, wherein the mode of administration of Idebenone is oral.

12. The method of claim 6, wherein the mode of administration of Idebenone is transmucosal.

* * * * *